US012708314B1

(12) United States Patent
Duffy et al.

(10) Patent No.: US 12,708,314 B1
(45) Date of Patent: Aug. 18, 2026

(54) METHODS AND SYSTEMS FOR ANALYZING ECG SIGNALS USING NEURAL NETWORKS

(71) Applicant: NeuralCloud Solutions Inc, Calgary (CA)

(72) Inventors: John Paul Duffy, Toronto (CA); Esmatullah Naikyar, Edmonton (CA); Michael Feist, St. Albert (CA)

(73) Assignee: NeuralCloud Solutions Inc., Toronto (CA)

( * ) Notice: Subject to any disclaimer, the term of this patent is extended or adjusted under 35 U.S.C. 154(b) by 0 days.

(21) Appl. No.: 18/896,784

(22) Filed: Sep. 25, 2024

Related U.S. Application Data

(60) Provisional application No. 63/684,432, filed on Aug. 18, 2024.

(51) Int. Cl.

| | |
|---|---|
| ***A61B 5/00*** | (2006.01) |
| ***A61B 5/0245*** | (2006.01) |
| ***A61B 5/361*** | (2021.01) |
| ***A61B 5/366*** | (2021.01) |
| ***G06N 3/045*** | (2023.01) |
| ***G06N 3/094*** | (2023.01) |

(52) U.S. Cl.
CPC ............ *A61B 5/361* (2021.01); *A61B 5/0245* (2013.01); *A61B 5/366* (2021.01); *A61B 5/7232* (2013.01); *G06N 3/045* (2023.01); *G06N 3/094* (2023.01)

(58) Field of Classification Search
None
See application file for complete search history.

(56) References Cited

U.S. PATENT DOCUMENTS

| | | | |
|---|---|---|---|
| 12,465,266 | B1 | 11/2025 | Duffy et al. |
| 2008/0001735 | A1 | 1/2008 | Tran |
| 2017/0112401 | A1 | 4/2017 | Rapin et al. |
| 2019/0231207 | A1 | 8/2019 | Perschbacher et al. |

(Continued)

FOREIGN PATENT DOCUMENTS

| | | |
|---|---|---|
| CN | 112603328 A | 4/2021 |
| CN | 116153320 A | 5/2023 |

OTHER PUBLICATIONS

International Search Report and Written Opinion, mailed Dec. 3, 2025 for International Application No. PCT/CA2025/051082.

(Continued)

*Primary Examiner* — Sana Sahand
(74) *Attorney, Agent, or Firm* — Wolf, Greenfield & Sacks, P.C.

(57) ABSTRACT

Methods and systems for automated electrocardiogram (ECG) analysis using neural networks, enhancing the accuracy of beat-by-beat cardiac monitoring. The system utilizes a Generative Adversarial Network (GAN) and beat classifiers to analyze ECG data and detect conditions various beast properties of an ECG at a discrete level. Additional neural networks may be trained to detect beat based conditions such as premature atrial contractions (PACs) and premature ventricular contractions (PVCs). The GAN generates realistic ECG beats, while classifiers detect abnormalities. Additional transformers may be trained to detect rhythm based conditions such as AFib and Aflutter. Methods and Systems support real-time cardiac health insights and integrates with ECG devices for continuous monitoring, offering a robust solution for improving diagnostic accuracy.

19 Claims, 7 Drawing Sheets

(56) References Cited

U.S. PATENT DOCUMENTS

| | | | |
|---|---|---|---|
| 2021/0106281 A1 | 4/2021 | Tran et al. |
| 2025/0032030 A1 | 1/2025 | Duffy et al. |
| 2025/0311956 A1 | 10/2025 | Ellinor et al. |

OTHER PUBLICATIONS

Aziz et al., ECG-based machine-learning algorithms for heartbeat classification. Sci Rep. Sep. 21, 2021;11(1):18738. doi: 10.1038/s41598-021-97118-5.

Brown et al., Language models are few-shot learners. Proc 34th Intl Conf Neural Info Proc Sys. Dec. 6, 2020;159:1877-1901.

Devlin et al., BERT: Pre-training of Deep Bidirectional Transformers for Language Understanding. Proceedings of the 2019 Conference of the North American Chapter of the Association for Computational Linguistics: Human Language Technologies, vol. 1 (Long and Short Papers). Jun. 2, 2019;4171-4186. doi: 10.18653/v1/N19-1423.

Hassaballah et al., ECG Heartbeat Classification Using Machine Learning and Metaheuristic Optimization for Smart Healthcare Systems. Bioengineering (Basel). Mar. 28, 2023;10(4):429. doi: 10.3390/bioengineering10040429.

Jambukia et al., Classification of ECG signals using machine learning techniques: A survey. Computer Engineering and Applications (ICACEA), 2015 International Conference on Advances at Ghaziabad, India. 2015;714-721. doi: 10.1109/ICACEA.2015.7164783.

Joung et al., Deep learning based ECG segmentation for delineation of diverse arrhythmias. PLoS One. Jun. 13, 2024;19(6):e0303178. doi: 10.1371/journal.pone.0303178.

Kalyakulina et al., Lobachevsky University Electrocardiogramatabase (version 1.0.1). PhysioNet. Jan. 19, 2021. 6 pages. doi: 10.13026/eegm-h675.

Kalyakulina et al., LUDB: a new open-access validation tool for electrocardiogram delineation algorithms. IEEE Access. Sep. 16, 2020;8:186181-186190. doi: 10.1109/ACCESS.2020.3029211.

Kingma et al., Adam: A Method for Stochastic Optimization. Proceedings of the 3rd International Conference for Learning Representations. Jul. 23, 2015. 15 pages. doi: 10.48550/arXiv.1412.6980v8.

Kolhar et al., Deep learning hybrid model ECG classification using AlexNet and parallel dual branch fusion network model. Sci Rep. Nov. 6, 2024;14(1):26919. doi: 10.1038/s41598-024-78028-8.

Makowski et al., NeuroKit2: A Python toolbox for neurophysiological signal processing. Behav Res Methods. Aug. 2021;53(4):1689-1696. doi: 10.3758/s13428-020-01516-y. Epub Feb. 2, 2021.

Narotamo et al., Deep learning for ECG classification: A comparative study of 1D and 2D representations and multimodal fusion approaches. Biomed Signal Process Control. Jul. 2024;93:106141. doi: 10.1016/j.bspc.2024.106141.

Nemcova et al., Brno University of Technology ECG Quality Database (BUT QDB) version 1.0.0. PhysioNet. Jul. 22, 2020. 4 pages. doi: 10.13026/kah4-0w24.

Peimankar et al., DENS-ECG: A Deep Learning Approach for ECG Signal Delineation. arXiv. May 18, 2020. 15 pages. https://arxiv.org/pdf/2005.08689.

Radford et al., Language Models Are Unsupervised Multitask Learners. OpenAI Blog 1.8. 2019:9. 24 pages.

Ribeiro et al. CODE-15%: a large scale annotated dataset of 12-lead ECGs. Zenodo. Jun. 9, 2021. 11 pages. doi.org/10.5281/zenodo.4916206.

Staszak et al., From Data to Diagnosis: How Machine Learning is Changing Heart Health Monitoring. Int J Environ Res Public Health. Mar. 5, 2023;20(5):4605. doi: 10.3390/ijerph20054605.

Tan et al., Icentia11k Single Lead Continuous Raw Electrocardiogram Dataset (version 1.0). PhysioNet. Apr. 12, 2022. 5 pages. doi.org/10.13026/kk0v-r952.

Tan et al., Icentia11K: An Unsupervised Representation Learning Dataset for Arrhythmia Subtype Discovery. arXiv. Oct. 21, 2019. 10 pages. doi: 10.48550/arXiv.1910.09570.

Yang et al., HiFi-Codec: Group-residual vector quantization for high fidelity audio codec. arXiv. May 7, 2023. 6 pages. doi.org/10.48550/arXiv.2305.02765.

Zeghidour et al., SoundStream: An End-to-End Neural Audio Codec. IEEE/ACM Transactions on Audio, Speech, and Language Processing. Nov. 23, 2021;30:495-507. doi: 10.1109/TASLP.2021.3129994.

400

Retrieving a set of labeled ECGs from one or more databases

402

Generating vectors representing each segmented heartbeat of respective ECGs

404

Training the beat classifier based on generated vectors and labels and the associated labels

406

METHODS AND SYSTEMS FOR ANALYZING ECG SIGNALS USING NEURAL NETWORKS

PRIORITY INFORMATION

This application is a non-provisional application of Provisional Patent Application No. 63/684,432, filed on Aug. 18, 2024, entitled "Methods and Systems for Analyzing ECG Signals Using Neural Networks," which is incorporated herein by reference in its entirety.

TECHNICAL FIELD

The invention relates to the field of biomedical engineering and, more specifically, to systems and methods for the automated analysis and annotation of electrocardiogram (ECG) signals. More specifically, the invention relates to the application of neural networks in enhancing the accuracy and efficiency of ECG signal processing.

BACKGROUND

The need for continuous and accurate ECG monitoring has become increasingly critical in modern healthcare. Devices such as ECG Patches and Holter Monitors provide valuable data on cardiac activity over extended periods. However, the challenge lies in accurately analyzing the large volume of data collected, particularly in real-world environments where noise and artifacts often interfere with signal quality. Traditional de-noising techniques, while effective to some extent, often result in the loss of critical information or fail to distinguish between noise and true cardiac events.

To address these challenges, exemplary embodiments utilize neural network-based exemplary approaches that enhance the accuracy of ECG signal analysis. Exemplary embodiments allow a beat-by-beat analysis that not only filters out noise but also retains vital cardiac information. Exemplary embodiments allow for seamless integration with ECG Patches and Holter Monitors, enabling real-time monitoring and analysis of cardiac health in various settings

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the present disclosure will now be illustrated by way of example. It is expressly understood, however, that the drawings are for the purpose of illustration and description only and are not intended as a definition of the limits of the present disclosure. Embodiments of the present disclosure will now be described by way of example in association with the accompanying drawings in which.

SUMMARY

Figure 1:
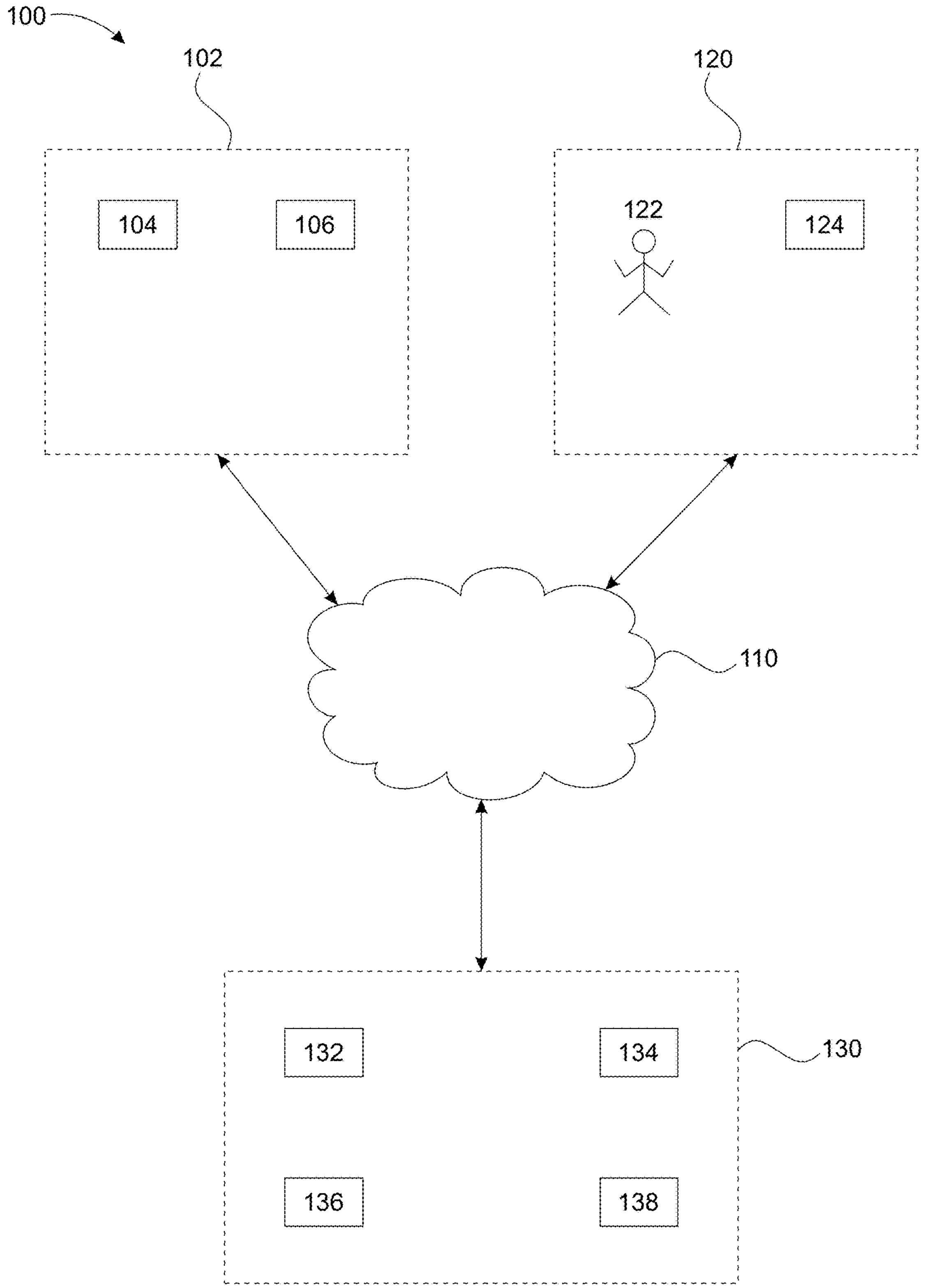
FIG. 1 shows a block diagram of an exemplary system for analyzing an ECG, consistent with one or more exemplary embodiments of the present disclosure.

This summary is intended to provide an overview of the subject matter of the present disclosure, and is not intended to identify essential elements or key elements of the subject matter, nor is it intended to be used to determine the scope of the claimed implementations. Its sole purpose is to present some concepts of one or more exemplary aspects in a simplified form as a prelude to the more detailed description that is presented later. The proper scope of the present disclosure may be ascertained from the claims set forth below in view of the detailed description below and the drawings.

One or more exemplary embodiments describe an exemplary method for a method for method for detecting health conditions based on an electrocardiogram (ECG), comprising training a general adversarial network and beat classifier, the general adversarial network comprising a generator and a discriminator network, the generator comprising an encoder, residual vector quantizer, and decoder, the discriminator network comprising a primary discriminator and a Fourier transform discriminator, the beat classifier comprising a neural network trained utilizing a supervised learning technique, wherein the encoder configured to receive an input and map it into a latent space via a series of convolutional layers and nonlinear activations, the residual vector quantizer configured to take the latent space representation and map it to a discrete set of quantized vectors through multiple stages of residual quantization, and the decoder configured to receive the quantized latent vectors and reconstruct generated ECG using transposed convolutional layers. The method includes the training comprising receiving, by one or more processors, a dataset of ECG data, creating, by the one or more processors, creating a set of individual heartbeats by segmenting each of the ECGs in the dataset of ECG data into singular beats, using segmented heartbeats from the ECG data as input to the generator to produce a set of generated heartbeats, training the generator to generate realistic ECG beats by minimizing the difference between generated and real ECGs based on feedback from both the primary discrimination and the Fourier transform discriminator, wherein the residual vector quantizer refines the output of the generator by quantizing residual errors at each stage of training, training the discriminators to distinguish between real and generated ECG beats based on the output of the decoder, and using the generator's output and feedback from the discriminators to iteratively improve the generator's accuracy in generating ECG beats, receiving, using one of more processors, a set of labeled ECGs for the supervised learning of the beat classifier, the labeled ECGs comprising labels of five or more of Q wave: peak, R wave: peak, S wave: peak, T wave: onset, peak, and offset, U wave: peak and offset, and QRS complex: onset and offset, segmenting each respective heartbeat in each ECG of the set of labeled ECGs and generating quantized vectors for each respective heartbeat utilizing the residual vector quantizer. The method further comprises training the beat classifier by inputting the quantized vectors for each respective heartbeat and associated labels for the respective heartbeat and iteratively minimizing a loss function that measures a difference between the predicted beat characteristic and the labeled beat characteristics, and updating beat classifier parameters using backpropagation during training to optimize classification accuracy for each characteristic. The method further comprises training a beat condition classification model differentiating between normal and abnormal heart conditions, wherein the clinical model evaluating normalcy, premature atrial contraction (PAC), and premature ventricular contraction (PVC), wherein the beast condition classification model is a neural network trained using supervised learning, the supervised learning comprising receiving a second labeled dataset of ECG data, the second labeled dataset including ECG signals labeled with specific beat types, including normal beats, premature atrial contractions (PAC), and premature ventricular contractions (PVC), training the beat condition classification model by minimizing a loss function that measures the difference between the predicted beat condition and the labeled beat condition in the second labeled dataset, and updating beat condition classification model parameters using backpropagation during training to optimize classification accuracy for each beat condition. The method further comprises determining beat-based conditions in an ECG, comprising receiving candidate ECG, by one or more processors, creating a candidate set of individual heartbeats by segmenting, using the one or more processors, the candidate ECG into singular beats, generating quantized vectors for each individual heartbeats in the candidate set of individual heartbeats by applying the residual vector quantizer, classifying beat properties of each individual heartbeat in the set of individual heartbeats of the candidate ECG by applying the beat classifier based on the generated quantized vectors for each for each individual set of heartbeats, the beat properties including five or more of Q wave: peak, R wave: peak, S wave: peak, T wave: onset, peak, and offset, U wave: peak and offset, and QRS complex: onset and offset, and determining presence of a clinical condition by applying the beat condition classification model on the classified beat properties, the clinical condition comprising one of normalcy, premature atrial contraction, and premature ventricular contraction, and applying a clinical solution based on presence of the clinical condition.

One or more exemplary embodiments describe an exemplary method for a method for classifying cardiac rhythms in electrocardiogram (ECG) data, the method comprising training a rhythm classifier, the rhythm classifier comprising a transformer, the transformer comparing a deep learning architecture, the training comprising receiving, by one or more processors, a dataset of ECG data labeled with corresponding rhythm types, the rhythm types including normal sinus rhythm, atrial fibrillation, and atrial flutter. The method may further comprise creating, by the one or more processors, a set of individual heartbeats by segmenting each of the ECGs in the dataset of ECG data into singular beats, and then quantized vectors representing each of the set of individual heartbeats utilizing a residual vector quantizer of a trained generator, comprising applying the residual vector quantizer to the set of individual heartbeats, the vector quantizer trained to compress and encode data into a lower-dimensional discrete space, creating positional encoded ECG data by applying, by the one or more processors, positional encoding to the quantized vectors to encode positional information for each individual heartbeat of the set of individual heartbeats in a sequence, processing the positional encoded ECG data through a multi-head self-attention mechanism to compute attention scores between each beat and other beats in the sequence, wherein the attention mechanism utilizes Query, Key, and Value vectors to capture temporal dependencies between the individual heartbeats, processing the positional encoded ECG data through a multi-head self-attention mechanism to compute attention scores between each beat and other beats in the sequence, wherein the attention mechanism utilizes Query, Key, and Value vectors to capture temporal dependencies between the individual heartbeats, concatenating outputs from multiple attention heads and applying a linear transformation to generate a transformed representation of the ECG sequence, passing the transformed representation through a feed-forward network comprising one or more layers to refine rhythm-based features, and optimizing model parameters based on a comparison between the predicted rhythm classifications and ground truth rhythm labels in the dataset, wherein the rhythm classifications include normal sinus rhythm, atrial fibrillation, and atrial flutter.

The method may further comprise classifying a candidate ECG, comprising, receiving, by the one or more processors, candidate ECG data representing a plurality of beats, creating, by the one or more processors, a set of candidate individual heartbeats by segmenting the candidate ECG data into singular beats, generating a candidate set of quantized vectors for the set of candidate individual heartbeats by applying the residual vector quantizer on the set of candidate individual heartbeats, generating positional encoded sequence by applying positional encoding to the candidate set of quantized vectors, generating a transformed representation of the set of quantized vectors by processing the positional encoded sequence through the trained rhythm classifier, and classifying the rhythm of each individual heartbeat in the input sequence of ECG data based on the transformed representations and the rhythm classifier, wherein the classifying includes classifying the rhythm as normal sinus rhythm, atrial fibrillation, or atrial flutter.

DETAILED DESCRIPTION

The novel features which are believed to be characteristic of the present invention, as to its structure, organization, use and method of operation, together with further objectives and advantages thereof, will be better understood from the following discussion.

As a preliminary matter, some of the figures describe concepts in the context of one or more structural components, variously referred to as functionality, modules, features, elements, etc. The various components shown in the figures can be implemented in any manner, for example, by software, hardware (e.g., discrete logic components, etc.), firmware, and so on, or any combination of these implementations. In one embodiment, the various components may reflect the use of corresponding components in an actual implementation. In other embodiments, any single component illustrated in the figures may be implemented by a number of actual components. The depiction of any two or more separate components in the figures may reflect different functions performed by a single actual component. The figures discussed below provide details regarding exemplary systems that may be used to implement the disclosed functions.

Some concepts are described in the form of steps of a process or method. In this form, certain operations are described as being performed in a certain order. Such implementations are exemplary and non-limiting. Certain operations described herein can be grouped together and performed in a single operation, certain operations can be broken apart into plural component operations, and certain operations can be performed in an order that differs from that which is described herein, including a parallel manner of performing the operations. The operations can be implemented by software, hardware, firmware, manual processing, and the like, or any combination of these implementations. As used herein, hardware may include computer systems, discrete logic components, such as application specific integrated circuits (ASICs) and the like, as well as any combinations thereof.

As to terminology, the phrase "configured to" encompasses any way that any kind of functionality can be constructed to perform an identified operation. The functionality can be configured to perform an operation using, for instance, software, hardware, firmware and the like, or any combinations thereof.

As utilized herein, terms "component," "system," "client" and the like are intended to refer to a computer-related entity, either hardware, software (e.g., in execution), and/or firmware, or a combination thereof. For example, a component can be a process running on a processor, an object, an executable, a program, a function, a library, a subroutine, and/or a computer or a combination of software and hardware.

By way of illustration, both an application running on a server and the server can be a component. One or more components can reside within a process and a component can be localized on one computer and/or distributed between two or more computers. The term "processor" is generally understood to refer to a hardware component, such as a processing unit of a computer system.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any non-transitory computer-readable device, or media.

Non-transitory computer-readable storage media can include but are not limited to magnetic storage devices (e.g., hard disk, floppy disk, and magnetic strips, among others), optical disks (e.g., compact disk (CD), and digital versatile disk (DVD), among others), smart cards, and flash memory devices (e.g., card, stick, and key drive, among others). In contrast, computer-readable media generally (i.e., not necessarily storage media) may additionally include communication media such as transmission media for wireless signals and the like.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In an exemplary embodiment, exemplary methods and systems allow for utilizing a brief electrocardiogram (ECG) signal for efficient cardiac monitoring, even on a beat-to-beat basis, and therefore does not require prolonged exposure. That is, exemplary systems and methods provide insight into cardiac health, and allow for instantaneous detection of cardiac anomalies, aiding in enhancing patient outcomes. In an exemplary embodiment, an ECG may be a European data file format.

In an exemplary embodiment, exemplary systems and methods first comprise approaches to train a Generative Adversarial Network (GAN) which is a type of machine learning model composed of two neural networks: a generator and a discriminator, which may be specifically trained simultaneously in a competitive setting. The goal of an exemplary GAN may be for an exemplary generator to produce generated ECGs that are indistinguishable from real ECGs, while an exemplary discriminator's role may be distinguish between real ECGs and generated ECGs that may be generated by the generator. In an exemplary embodiment, this adversarial process may lead to an exemplary generator improving its outputs over time, producing highly realistic data. In an exemplary embodiment, exemplary generator may include an encoder, residual vector quantizer, and decoder. In an exemplary embodiment, once an exemplary GAN is trained, quantized vectors may be generated during inference which may accurately represent and provide insight into each heartbeat of an ECG.

Exemplary methods may further include training a beats classifier and a rhythm classifying model, which may be both trained models utilizing supervised approaches. For example, labels for beats classifiers may entail utilizing labeled beat features, such as PQRST, onset/offset, etc., within each heartbeat. In an exemplary embodiment, this may be done by utilizing supervised machine learning, wherein data associated with ECGs are input where these properties have been labelled by experts or utilizing labeling techniques. In an exemplary embodiment, each ECG may be labeled for peaks for the PQRST waveform, duration of the P wave including the start and the end (which may be referred to as P onset and P offset), start and end of the QRS complex marked as an exemplary onset and offset (which may be referred to as Q onset and J-Point respectively), and duration of T waves, where an exemplary start of a T wave maybe an exemplary end of an ST segment.

In an exemplary embodiment, additional machine learning models may then be trained and later utilized to determine presence of heart related conditions based on classification of beats by an exemplary beast classifier.

In an exemplary embodiment, utilizing an exemplary trained generator, an exemplary machine learning model may be trained to rhythm-based conditions in an exemplary ECG, such as AFib or Aflutter.

Accordingly, in an exemplary embodiment, quantized vectors generated by a trained generator based on exemplary ECG signals may be utilized to generate detailed reports on cardiac health, including PQRST intervals, heart rate (HR), heart rate variability (HRV), and other key metrics. In an exemplary embodiment, machine learning models may be generated utilized supervised learning techniques to generate CSV files which may provide insight on a beat-to-beat levels including providing detailed annotations, including PQRST intervals, HR, HRV, and other cardiac metrics. In an exemplary embodiment, machine learning models may be utilized to generate comprehensive statistical reports that provide insights into the patient's cardiac health over the monitoring period. In an exemplary embodiment, in addition to CSV, sample reports and files may be generated containing beat-to-beat data, charts, analysis, and statistics.

Referring now to the figures, FIG. 1 shows a block diagram of an exemplary system 100 for cardiac conditions based on ECG, consistent with one or more exemplary embodiments of the present disclosure. In an exemplary embodiment, system 100 includes a healthcare facility environment 102, network 110, physician environment 120, and service provider environment 130.

One of ordinary skill in the art would recognize that any of the elements of health care facility environment 102 and physician environment 120 may be present in the other, or they may simply function as a singular environment.

In an exemplary embodiment, health care facility environment 102 may include ECG device 104. In an exemplary embodiment., health care facility environment may further contain processors 106 and databases 108. In an exemplary embodiment, databases 108 may be utilized to store information and data including medical records, health records, billing, ECGs, etc. In an exemplary embodiment, processors 106 may be utilized for communicating with external sources, managing health data, interaction with ECG device 104, and additional processes.

In an exemplary embodiment, all elements within system 100 may be connected to an electronic network 100, such as the Internet, through one or more computers, servers, and/or handheld mobile devices.

In an exemplary embodiment, physician environment 120 physician 122 may retrieve ECGs. Furthermore, in an exemplary embodiment physician 122 may also obtain any combination of patient-specific information, such as age, medical history, blood pressure, blood viscosity, etc. Combination of processors 124 and databases 126 that are part of physician environment may be utilized to enter and store medical records, transmit information/data, communicate with external entities, view reports, request medical reports, send prescriptions, and/or send instructions to patients.

In an exemplary embodiment, physician 122 or an entity may transmit medical data (for example, ECGs) and/or patient-specific information to service provider environment 130, along with a request for analytical reports.

In an exemplary embodiment, service provider environment 130 may have databases 132 for storing data, including data for storing received from physician 122 or any other sources. In an exemplary embodiment, databases 132 may further store models generated utilizing artificial intelligence which may be constantly updated and may be utilized to evaluate additional data received by processors 134. Furthermore, service provider environment 130 may further include processors 134 which may comprise processing devices for processing medical data stored in the storage devices. In an exemplary embodiment, service provider environment 130 may provide a physician, an ERM, or other entity with a health report which may include an exemplary insight based on received medical data (ECGs) for evaluation.

Figure 2A:
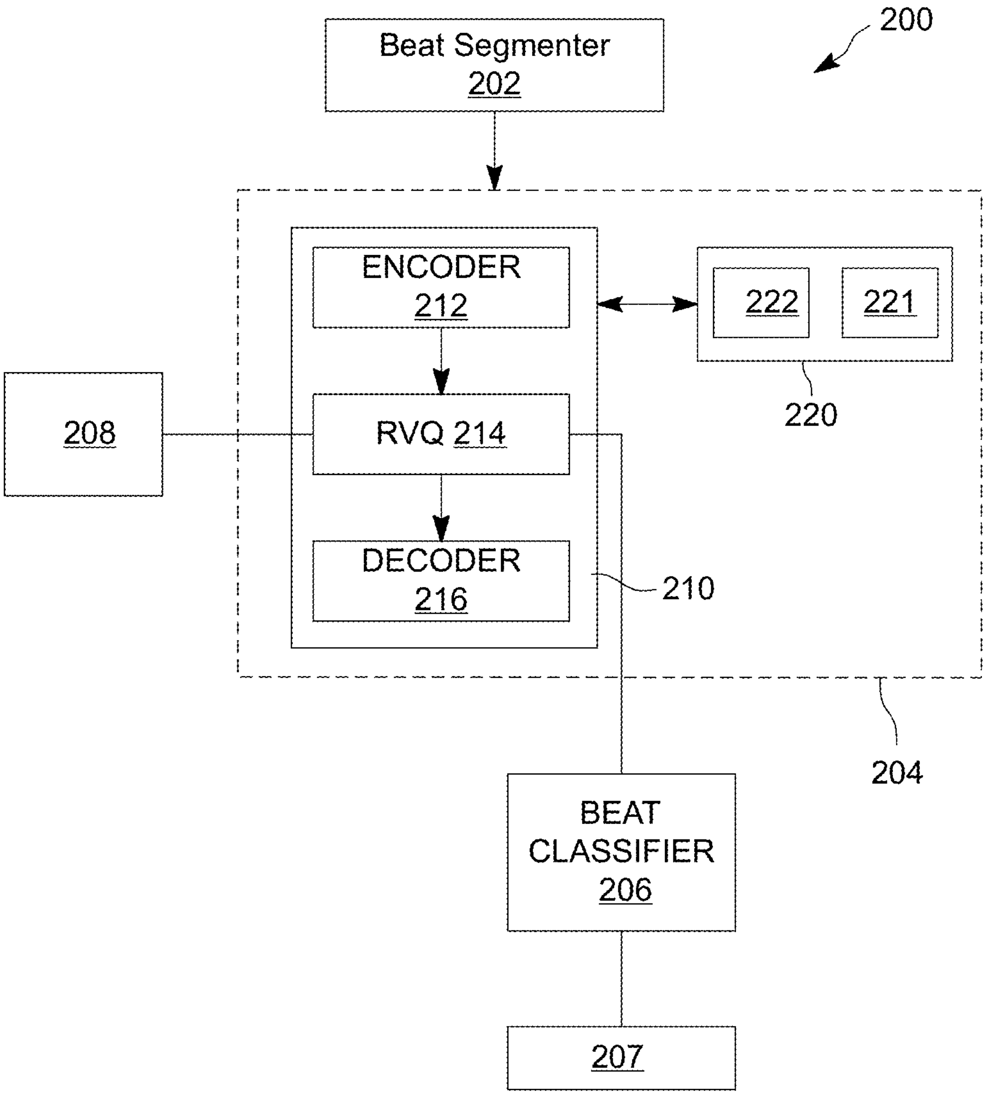
FIGS. 2A-C show an exemplary machine learning model structure for analyzing an ECG, consistent with one or more exemplary embodiments of the present disclosure.
Figure 2B:
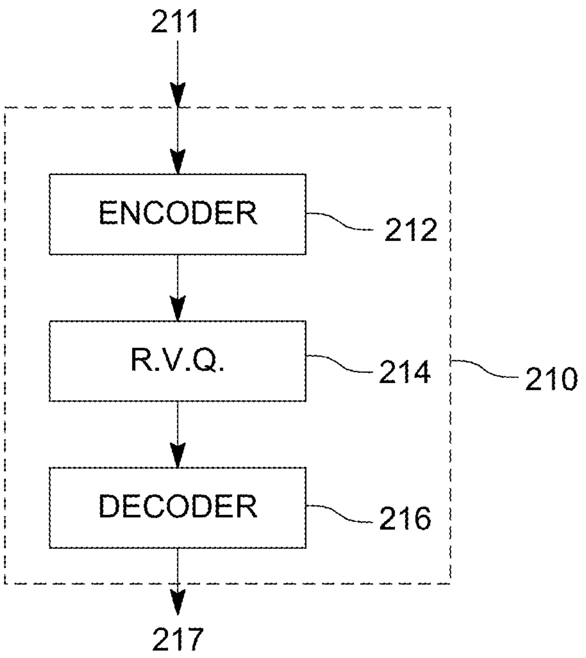
Figure 2C:
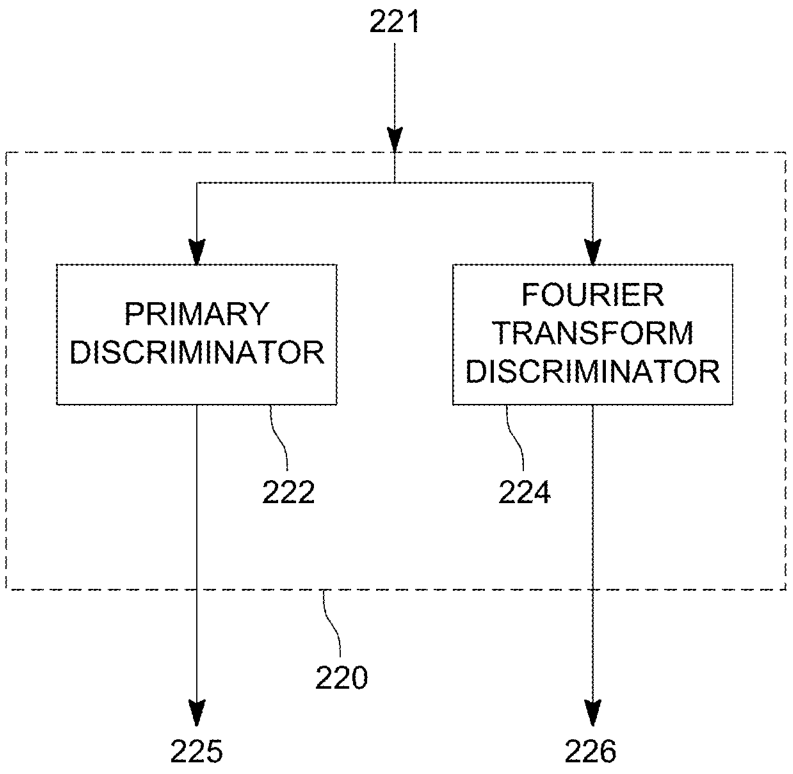

Referring now to the figures, FIG. 2A-C show an exemplary machine learning model structure 200 for analyzing an ECG, consistent with one or more exemplary embodiments of the present disclosure. As illustrated in FIG. 2A, an exemplary structure may comprise a beat segmenter 202, a GAN 204, a beat classifier 206, beat condition detection model 207, and rhythm classifier 208.

Figure 3:
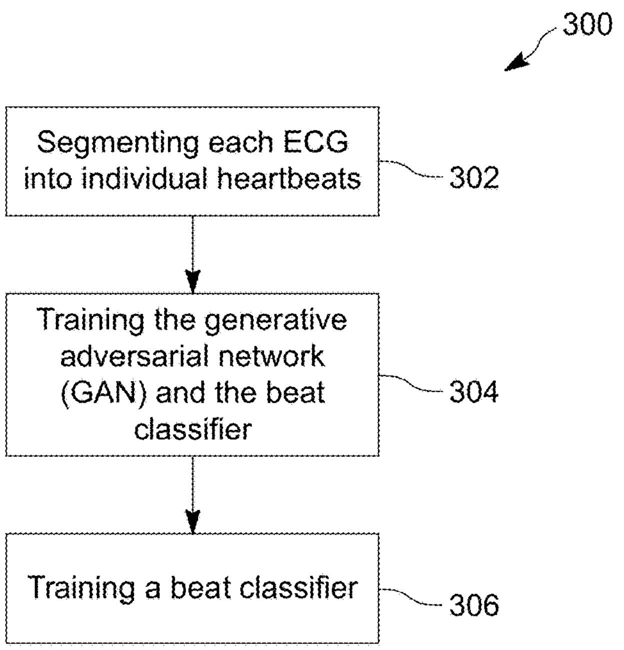
FIG. 3 illustrates a flowchart for a method for training a generative adversarial network (GAN) and a beat classifier, consistent with one or more exemplary embodiments of the present disclosure.

For furthering the understanding of machine learning model structure 200, FIG. 3 provides an exemplary flowchart for a method 300 for training a GAN and a beats classifier, consistent with one or more exemplary embodiments of the present disclosure.

In an exemplary embodiment, an exemplary beat segmenter 202 may refer to one or more processors or an exemplary machine learning model trained to utilize Shannon's entropy for ECG beat segmentation. In an exemplary embodiment, beat segmentation may involve calculating the entropy across an exemplary ECG signal in sliding windows and then using those entropy values to locate key features like the QRS complex, which can be used to identify and segment individual heartbeats. In an exemplary embodiment, when a peak is determined, a sample may be taken between exemplary peaks. Furthermore, a sample may be taken based on a time distance on either side of a respective peak, for example, a second long duration around an exemplary peak. Accordingly, in an exemplary embodiment, an exemplary beat segmenter 202 may segment an exemplary ECG into a plurality of individual heartbeats (HB) which when put together may allow for reconstruction of an exemplary ECG. Exemplary embodiments utilize segmented individual heartbeats both in training and inference across all exemplary machine learning models to provide granular insights into health conditions.

In context of FIG. 3, step 302 may comprise segmenting each ECG into individual heartbeats. In an exemplary embodiment beat segmenter 202 as described above may be utilized to segment each respective ECG into individual heartbeats.

In an exemplary embodiment, step 304 may comprise training the GAN and the beat classifier.

Returning to FIG. 2A, in an exemplary embodiment, exemplary GAN 204 comprising generator 210 and discriminator network 220 may be trained first, along with beat classifier 206. FIGS. 2B and 2C illustrate the details of GAN 204. In an exemplary embodiment, during batches consisting of 64, 128, or another number of batches may be provided iteratively to neural network being trained at any time. For example, whether generator 210, discriminator 220, or beat classifier 206 is being trained, it may respectively receive a batch of data (related to segmented heartbeats from an ECG).

In an exemplary embodiment GAN 204 may refer to a Generative Adversarial Network (GAN) which is type of machine learning model composed of two neural networks: a generator and a discriminator, which are trained simultaneously in a competitive setting. In an exemplary embodiment, an exemplary goal of GAN 204 is for the generator 210 to produce synthetic data that is indistinguishable from real data (generated ECGs are indistinguishable from real ECGs), while the discriminator 220's role is to distinguish between real data and the synthetic data generated by generator 210. This adversarial process leads to generator 210 improving its outputs over time, producing highly realistic data.

Accordingly, in an exemplary embodiment, discriminator network 220 may only play a part during a training phase of GAN 204 to help refine functioning of aspects of generator 210. Accordingly, during inference, only generator 210 or parts of generator 210 may be utilized. As illustrated in FIGS. 2A and 2B, in an exemplary embodiment, generator 210 may comprise of encoder 212, residual vector quantizer (RVQ) 214, and decoder 216. An input 211 into generator 210 may lead to output 217 from decoder 216. That is, based on any input, including an ECG beat, a clean generated beat may be output from decoder 216. In exemplary embodiment, one generator 310 is trained to generate output 217, quantized vectors from RVQ 214 may be utilized by exemplary models consistent with exemplary embodiments for various beat and rhythm-based analysis. Utilizing quantized vectors may allow for efficient data usage while capturing properties of EGG in an efficient manner. In an exemplary scenario, for example 64 heartbeats may be provided to an exemplary generator 210. In an exemplary embodiment, during training, noise may be added randomly to a few of the ECGs and may include random noise, white noise, spikes, drift, etc., that may be added to data related to some of the individual heart beats, that is, some of the inputted heartbeats to generator 210 would have ECGs as captured and some would have noise added. In an exemplary embodiment, this may allow for training of generator 210 to improve its ability to generate clean ECGs.

In an exemplary embodiment, encoder 212 may compress an exemplary input into a latent space representation, that is, an exemplary encoder may be configured to receive a noise input, ECG, or ECG with noise and map it into a latent space via a series of convolutional layers and nonlinear activations. In an exemplary embodiment, during training a set of segmented beats, that is, individualized heartbeats may be provided to encoder 212. In an exemplary embodiment, encoder 212 may be responsible for compressing an exemplary input (individualized heartbeats as captured or with noise added) into a lower-dimensional, compact representation, or latent code. In an exemplary embodiment, during training, encoder 212 encoder learns to extract essential features from an exemplary input that may be necessary for generating realistic data. In an exemplary embodiment, encoder may comprise of several convolutional layers and may be referred to as a convolutional neural network. In an exemplary embodiment, each convolutional layer may process an exemplary input through a series of nonlinear transformations to capture relevant features. In an exemplary embodiment, an exemplary output of encoder 212 may be a latent code, which is a compressed version of exemplary input data, encoding its most important features in a lower-dimensional space. For example, encoder 212 may map an input heartbeat from an ECG from a high-dimensional space into a lower-dimensional latent representation, using multiple convolutional layers with non-linear activation functions.

In an exemplary embodiment, RVQ 214 may receive an exemplary latent code from encoder 212 and may discretize the latent space into quantized vectors, refining the latent representation. In an exemplary embodiment, RVQ 214 may be configured to discretize an exemplary latent code generated by encoder 212 into a quantized version. In an exemplary embodiment, discretizing latent code may allow generator 210 to produce discrete latent variables that capture specific patterns in the data. In an exemplary embodiment, transforming the continuous latent space produced by encoder 212 into a quantized (discrete) space, thereby imposing structure on the latent variables and allowing for more control over the generated data. In an exemplary embodiment, RVQ 214 may take the latent code and map it to the closest codebook entries in a quantized space. In an exemplary embodiment, an exemplary quantization process may be done in stages (residual quantization), where successive layers refine the quantization by encoding residuals-differences between the input and its quantized version.

In an exemplary embodiment, an exemplary output of RVQ 214 may be quantized vectors (that is, a set of discrete latent variables) that may be passed to decoder 216 for reconstruction. In an exemplary embodiment, other elements of machine learning model structure 200 may utilize quantized vectors from RVQ 214 because it may compress high-dimensional latent representation into a more compact quantized vector, with the reduced dimensionality making it easier for additional neural networks to process any inputs, requiring fewer computational resources while retaining key feature. In an exemplary embodiment, once RVQ 214 is trained, utilizing its outputs for faster training and inference times for additional neural networks within machine learning model structure 200. In an exemplary embodiment, exemplary approaches allow for faster inference while minimizing computational resources, which aid in providing detailed beat-to-beat analysis based on an ECG.

In an exemplary embodiment, decoder 216 may reconstruct a generator beat output from quantized vectors of RVQ 214. In an exemplary embodiment, decoder 216 may be configured to reconstruct a generated beat output (such as a reconstructed individual beat which may be presumed to be a clean beat free of any noise) as an output based on quantized vectors provided by RVQ 214. In an exemplary embodiment, as will be described in further detail below, clean beats that may be output by decoder 216 may be provided to discriminator network 220 during training of GAN 204.

In an exemplary embodiment, decoder 216 may be configured to take quantized vectors from RVQ 214 and up sample it back into the original high-dimensional data space, effectively generating an exemplary output that may mimic real data. In an exemplary embodiment, decoder 216 may utilize a convolutional neural network as well and may utilize deconvolutional or transposed convolutional layers) to progressively upscale and refine the latent code into a detailed, high-resolution output. In an exemplary embodiment, an exemplary output of generator 216 may be an exemplary generated clean ECG beat which may be synthetic data sample, that resembles an ECG (the real data) which generator 210 aims to emulate. For example, decoder 216 may take the quantized latent code or quantized vectors and may process it through a series of upsampling layers (e.g., transposed convolutions) to generate a clean beat.

In an exemplary embodiment, during training of an exemplary GAN 204, discriminator network 220 directly influences how generator 210 learns to produce more realistic data. As illustrated in FIGS. 2A and 2C, in an exemplary embodiment, discriminator network 220 may comprise of both primary discriminator 222 and Fourier transform discriminator 224. In an exemplary embodiment, input 221 provided to discriminator network 220 may be provided to primary discriminator 222 and Fourier transform discriminator 224. As described in further detail below, a Fourier transform may be applied to input 221 before it is evaluated by Fourier Transform Discriminator 224. In an exemplary embodiment, based on input 221 which may be a real ECG or an exemplary generated ECG (by generator 210, that is, output 217), primary discriminator 222 and Fourier transform discriminator 224 may each provide output 225 and output 226 respectively. In an exemplary embodiment, output 225 and output 226 may represent primary discriminator 222's and Fourier transform discriminator 224's determination of whether input 216 was a real or a generated ECG. In an exemplary embodiment, output 225 and output 226 may be provided in form of a 0 or 1. In an exemplary embodiment, since, real ECGs and generated ECGs are fed to discriminator network 220, and it is known what primary discriminator 222 and Fourier transform discriminator 224 are evaluating, an exemplary comparator (not shown) may utilize output 225 and output 226 (representing exemplary discriminator predictions) with actual known data to evaluate accuracy of the predictions of exemplary discriminators. Details regarding providing feedback based on this evaluation is described in further detail below.

In an exemplary embodiment, generator 210 and discriminator network 224 in GAN 204 may operate in an adversarial setup. In an exemplary embodiment, goal of generator 210 may be to produce data so realistic that the discriminators 222 and 224 cannot distinguish it from real data, that is, can not differentiate between a real ECG and a generated ECG. Accordingly, in exemplary GAN 204, an exemplary two-part discriminator network 220 (primary discriminator 222 and Fourier transform discriminator 224) plays a crucial role in refining the generator's ability to create increasingly high-quality data.

In an exemplary embodiment, primary discriminator 222 and Fourier transform discriminator are fed either real or generated ECGs and provide feedback to generator 210 on whether it is realistic. In further detail, primary discriminator 222 may ECGs (including generator 210's outputs) which may comprise ECG beats in the time or spatial domain (i.e., raw data), providing feedback to generator 210 on whether its samples appear realistic when compared to real ECGs. In an exemplary embodiment, this may be done by providing discriminator network 220 with two sets of associated data, a set of real (clean) ECGs and a set of generated ECGs. In an exemplary embodiment, each of clean and generated ECGs may be fed to an exemplary discriminator within discriminator network 220. Based on comparison of between expected results of an exemplary discriminator and actual status ECG (whether it is real or generated), weights within an exemplary discriminator may be changed. In detail, discriminator 220's task is to classify each ECG input as either real or generated. Based on the comparison between the expected results (whether the ECG is classified correctly as real or generated) and the actual status of the ECG (whether it truly is real or generated), the weights within the discriminator network are updated through backpropagation. Specifically, when the discriminator makes a wrong prediction (e.g., classifying a generated ECG as real or vice versa), the error is propagated backward through the network, adjusting the weights using a gradient descent algorithm. The amount by which each weight is changed depends on the magnitude of the error and the learning rate. By iteratively adjusting the weights in this manner, the discriminator becomes more accurate in distinguishing between real and generated ECGs over time.

In an exemplary embodiment, if primary discriminator 222 classifies a generated ECG as fake, it signals to the generator that the sample lacks key features present in real ECGs. Accordingly, generator 210 then adjusts its weights during backpropagation to produce outputs of ECGs that better match the clean data, thereby "fooling" primary discriminator 222 in future iterations.

In an exemplary embodiment, in details with regards to an exemplary training feedback loop, an exemplary generator produces generated ECGs. In an exemplary embodiment, primary discriminator 222 evaluates generated ECGs, comparing it to real ECGs and providing feedback based on its classification score.

In an exemplary embodiment, generator 210 may update its parameters to reduce the discrepancy between generated and real data, that is, generated ECGs and real ECGs. In an exemplary embodiment, this may optimize to minimize the loss function driven by the primary discriminator's classification.

In an exemplary embodiment, Fourier transform discriminator 224 may provide additional, deeper feedback by assessing the generator's outputs in the frequency domain. In an exemplary embodiment, generated ECGs might initially fool primary discriminator 222, but the Fourier transform discriminator 224 may detect discrepancies in the frequency characteristics of generated ECGs versus real ECGs (such as subtle patterns, artifacts, or noise in certain frequency ranges).

In an exemplary embodiment, similar to receiving feedback from primary discriminator 222, by receiving feedback from Fourier transform discriminator 224, generator 210 learns to not only produce ECGs that look realistic in spatial domain but also conforms to the frequency characteristics of real ECGs. In an exemplary embodiment, this may push generator 210 to refine its outputs comprising generated ECGs further, ensuring that they appear authentic across both domains. In an exemplary embodiment, Fourier transform discriminator 224's weights may be changed similarly to primary discriminator 222's using back propagation and error calculation.

In an exemplary embodiment, in context of training an exemplary GAN, such as GAN 204, generator 210 may produce generated ECGs which may be passed to Fourier transform discriminator 224 after undergoing a Fourier transform. In an exemplary embodiment, Fourier transforms may be applied utilizing one or more processors and algorithms known in the art that allow Fourier transforms to be applied to data. In an exemplary embodiment, one or more processors, may utilize an exemplary algorithms or process that may apply Fourier transforms to data, that is, Fourier transform may be applied to real ECG or generated ECGs provided to discriminator network 220.

In an exemplary embodiment, Fourier transform discriminator 224 may then evaluate data Fourier transformed data and may provide feedback on whether the frequency components of the generated ECGs match those of real ECGs.

In an exemplary embodiment, generator 210 may use this additional feedback to fine-tune its parameters, learning to generate ECGs that mimics both the spatial and frequency features of a real ECG.

Accordingly, in an exemplary embodiment, an exemplary generator, such as generator 210 may be trained to minimize a loss function that considers the feedback from both discriminators. Specifically: generator 210 may learn to produce ECGs that pass visual/spatial scrutiny by primary discriminator 222 and may focus on creating outputs that resemble the structure, texture, and features of real ECGs when analyzed in their raw form. In an exemplary embodiment, based on Fourier Transform Discriminator 224, generator 210 may learn to match frequency patterns of real ECGs, correcting subtle frequency artifacts that might not be apparent in the raw domain but are detectable through a Fourier analysis.

In an exemplary embodiment, loss function for generator 210 may combine the feedback from both discriminators 222 and 224 within discriminator network 220. In an exemplary embodiment, generator 210 may be penalized for generating data (ECGs) that primary discriminator 222 identifies as fake. In an exemplary embodiment, generator 210 may also be penalized for generating data (ECGs) that may have incorrect frequency characteristics, as identified by the Fourier transform discriminator 224.

In an exemplary embodiment, generator 210 may optimize itself by minimizing the combined loss from both discriminators. In an exemplary embodiment, this forces generator 210 to improve across multiple dimensions—spatial and frequency—ensuring higher-quality, more realistic outputs.

In an exemplary embodiment, for insight into an exemplary scenario, generator may produce an exemplary data sample, that is, an exemplary generated ECG. In an exemplary embodiment, an exemplary ECG may then be passed through primary discriminator 222, which may classify it as real or fake based on spatial or time-domain features. In an exemplary embodiment, primary discriminator 222 may provide feedback (classification score), and generator 210 may update its weights based on an error signal that may be backpropagated through generator 210.

In an exemplary embodiment, an exemplary ECG may undergo a Fourier transform, converting it into the frequency domain. In an exemplary embodiment, transformed data may be fed into the Fourier transform discriminator 224, which may evaluate the frequency characteristics and provides its own feedback (classification score). In an exemplary embodiment, generator 210 may update its parameters based on this second source of feedback.

In an exemplary embodiment, generator 210 may combine both sets of feedback to adjust its internal weights. In an exemplary embodiment, as generator 210 improves, it learns to generate data that not only looks realistic in the raw domain but also exhibits the proper frequency characteristics, increasing its ability to "fool" both discriminators 222 and 224.

In an exemplary embodiment, by having two exemplary discriminators, that is, primary discriminator 222 and Fourier transform discriminator 224, one operating in the spatial domain and one in the frequency domain—generator 210 learns to produce higher-quality synthetic data that looks real not only in its appearance but also in its underlying frequency properties. In an exemplary embodiment, this exemplary dual-discriminator approach may lead to a more robust and sophisticated training process for generator 210, helping it refine its outputs to match the complexity of real-world data more closely.

In an exemplary embodiment, generator 210's goal may be to minimize the loss function, which may measure how well data generated by generator 210 fools an exemplary discriminator, such as discriminators within discriminator network 220. In an exemplary embodiment, the loss function used for generator 210 may be the negative of an exemplary discriminator's output when fed the generated data. In an exemplary embodiment, an exemplary GAN loss function $L_G$ for generator 210 may be:

$$L_G = -\log(D(G(z))) \quad \text{(Equation No. 1)}$$

where, G(z) is the generator's output based on an input z, D(G(z)) is the discriminator's output, representing the probability that G(z) is real. In an exemplary embodiment, generator 210 may be updated to maximize D(G(z)), meaning it aims to increase discriminator network 220's belief that the generated data is real.

In an exemplary embodiment, generator 210's weights may be updated gradient descent using the backpropagation algorithm. In an exemplary embodiment, weight update may be updated as:

$$\theta_G \leftarrow \theta_G - \eta\backslash frac\{\partial L_G\}\{\partial \theta_G\} \quad \text{(Equation No. 2)}$$

where $\theta_G$ is the weights (parameters) of generator 210, η is the learning rate, and \frac{∂LG$_G$}{∂θG} represents the gradient of the generator 210's loss function $L_G$ with respect to its weights. Accordingly, in an exemplary embodiment, this exemplary rule may adjust generator 210's weights by calculating the gradient of the loss function with respect to the generator's weights and applying a small update in the direction that minimizes the loss.

In an exemplary embodiment, trained generator 210 may be used for inference in numerous instances and for training additional machine learning models within the machine learning model structure.

In an exemplary embodiment, generator 210 may trained not only to minimize the adversarial loss but also to reduce the quantization error introduced by RVQ 214 in an exemplary RVQ process. In an exemplary embodiment, RVQ 214 plays a critical role by mapping the latent space representations to a discrete set of quantized vectors, with each quantization stage progressively reducing the residual error between the original latent representation and the quantized version. During training, 214 RVQ refines the output of generator 210 by iteratively quantizing the residual errors at each stage. This quantization process ensures that key features of the ECG signal are preserved while compressing the data, enabling efficient downstream processing. In an exemplary embodiment, generator 210's weights may therefore be updated during training via backpropagation, based on a loss function that accounts for both the adversarial loss and the residual quantization error. As discussed above, adversarial loss may calculated based on feedback from discriminator network 220, which attempts to distinguish between real ECG data and the generated ECG data. Simultaneously, residual quantization error may be calculated as the difference between the original latent vector and the quantized vector at each stage of quantizing process by RVQ 214.

In an exemplary embodiment, by combining these two objectives—minimizing the adversarial loss and minimizing the residual quantization error—generator 210 may produce highly realistic ECG beats that not only fool the discriminator network 220 but also exhibit minimal quantization distortion. The generator's weights may be updated iteratively to optimize this combined loss function, ensuring that the generated ECG beats closely resemble real ECG signals while being represented in an efficient, quantized form.

In an exemplary embodiment, this dual loss function strategy may result generator 210 producing high-quality ECG beat representations that are suitable for both clinical evaluation and further classification, while also maintaining computational efficiency through the use of RVQ 214. In an exemplary embodiment, utilizing training RVQ 214 during the training process may enable generate 210 to balance realism and precision, as the quantized vectors may be used for downstream tasks such as beat classification and condition detection with minimal information loss.

In an exemplary embodiment, beat classifying model 206 comprises a model which may be a supervised model that may be utilized to characterize beat properties within each segmented heartbeat.

Figure 4A:
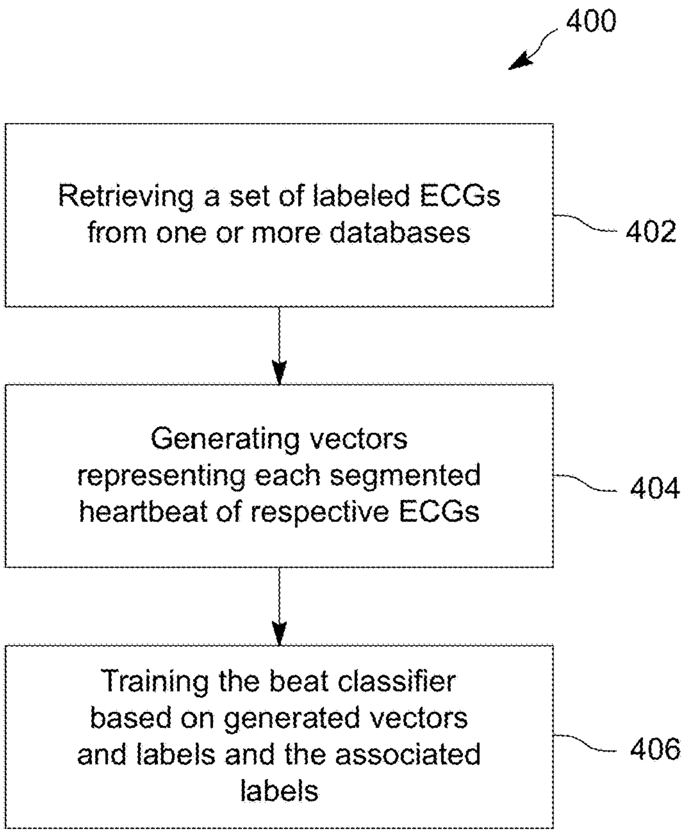
FIG. 4A illustrates a flowchart for a method for training a beat classifier, consistent with one or more exemplary embodiments of the present disclosure.

In an exemplary embodiment, step 306 of method 300 may comprise training a beat classifier. In an exemplary embodiment, FIG. 4A illustrates method 400, which outlines the training steps of step 306 in greater detail.

In an exemplary embodiment, step 402 may involve retrieving a set of labeled ECGs from one or more databases. In an exemplary embodiment, labels associated with each respective ECG may be manually entered by a qualified user—such as a technician or physician—using a physical device or an electronic interface. The labeling process is crucial for training an exemplary beats classifier or beats classifying model and may include detailed annotations of various ECG waveforms.

In an exemplary embodiment, each ECG may be labeled to capture key waveform peaks and durations, including:

P wave: onset, peak, and offset;
Q wave: peak;
R wave: peak;
S wave: peak;
T wave: onset, peak, and offset;
U wave: peak and offset; and
QRS complex: onset and offset.

In an exemplary embodiment, during training for each individualized segmented heartbeat, identifying the duration of the P wave, the QRS complex, and the T wave, where the start and end points of each waveform (e.g., P onset, Q onset, J-point, and T onset) may be critical for finding various conditions.

In an exemplary embodiment, step 404 may comprise generating vectors representing each segmented heartbeat of respective ECGS. In an exemplary embodiment, this may be achieved by utilizing beat segmenter 202, encoder 210, and residual vector quantizer 214. In detail, generating a beat classifier may entail leveraging the trained GAN 204, specifically RVQ 214 and labeled ECG data. That is, in the set of labeled ECGS, for each labeled ECG, it may first be segmented using beat segmented 202 and may then be provided to generator 204 so that RVQ 214 may produce a quantized vector for each heartbeat.

Step 406 may include training the beat classifier based on generated vectors and labels and the associated labels. In detail, an exemplary neural network may be provided quantized vectors representing the ECGs and the labels, as described above, allowing it to learn to predict key waveform components. By utilizing its predictions, and entered labels, beast classifier 206 may be trained to accurately generate labels for future ECGs. In an exemplary embodiment, beat classifier 206 may work towards iteratively minimizing a loss function that measures a difference between the predicted beat characteristic and the labeled beat characteristics, and updating beat classifier parameters using backpropagation during training to optimize classification accuracy for each characteristic. Accordingly, iteratively, as generator and discriminator are updated in each iteration, then for every batch of ECGs during training of beat classifier 206, an exemplary model is refined.

In an exemplary embodiment, beat classifier 206 may be trained to generate accurate labels for each of the key waveform components in the ECG, such as P wave onset, peak, and offset, QRS complex features like Q onset and J-point, and T wave onset, peak, and offset. In an exemplary embodiment, an exemplary training process may ensure that an exemplary model learns to precisely label these features by analyzing the embedding vectors generated from the labeled ECG data. In an exemplary embodiment, the goal may be to improve the model's ability to detect and label these critical features in unseen ECG. In an exemplary embodiment, based on an iterative process, beat classifier 206 which may be a supervised learning model may continue to aid in refining generator 204. That is, feedback may be provided based on predictions of beat classifier 206 in its training process for generator 210 to further refine its weights. Accordingly, in an exemplary embodiment, outputs of encoder 212, RVQ 214, and decoder 216, may inherently take into account variables that are associated or important for beat classifier 206 to classify aspects of a beat or beat properties during an iterative process.

In an exemplary embodiment, during an inference phase (that is, after beats classifier 206 has been trained), an exemplary trained beats classifier 206 may be used to label and classify new ECG data. As discussed above, any new ECG data may first be segmented by beat segmenter 202 and then may be provided to generator 210 so that RVQ 214 may generate an exemplary quantized vector utilizing exemplary codebooks. In an exemplary embodiment, exemplary quantized vector may then be utilized to apply learned feature representations by trained beats classifier 206 to accurately label the onset, peak, and offset of key waveforms, thereby providing diagnostic insight into heartbeat patterns.

In an exemplary embodiment, trained beat classifier 206 may be utilized for training additional models. For example, beat condition detection model 207 may be an exemplary model and trained neural network to detect an exemplary beat condition based on classification of exemplary beat traits by beat classifier 206. In an exemplary embodiment, an exemplary beat condition detection model 207 may focus solely on detecting medical conditions based on beat-level features extracted from ECG data. In an exemplary embodiment, exemplary beat condition classifying model 207 may model specifically addresses conditions such as normal beats, Premature Atrial Contractions (PACs), and Premature Ventricular Contractions (PVCs), In an exemplary embodiment, beat condition detection model 207 may additionally be trained to determine various additional cardiac conditions based on beat calculations. In an exemplary embodiment, this may include bradycardia, tachycardia, short PR interval, pauses, first-degree AV block with a prolonged PR interval greater than 200 ms, longest RR interval, pauses where the RR interval exceeds 3000 ms, long QT syndrome, second-degree Mobitz I (Wenckebach), second-degree Mobitz II, third-degree (complete) AV block, and atrial fabulation. All of these conditions may be detected and classified using the beat condition detection model 207, enabling comprehensive ECG analysis.

Figure 4B:
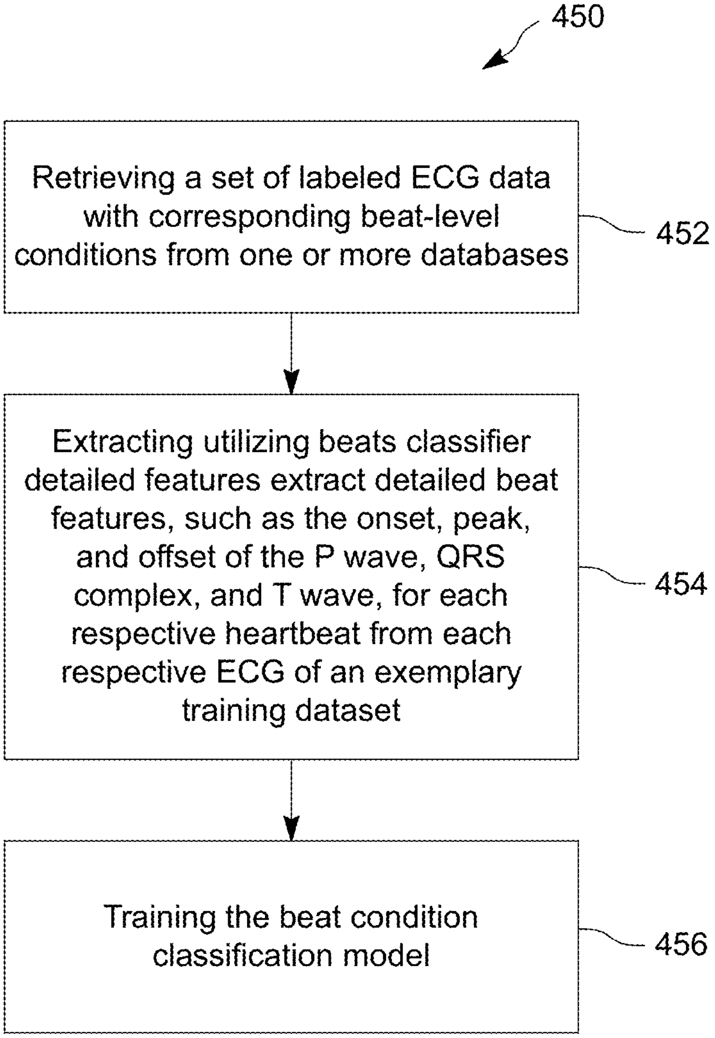
FIG. 4B illustrates a flowchart for a method for training a beat condition model, consistent with one or more exemplary embodiments of the present disclosure.

In an exemplary embodiment, training beat condition model may entail applying steps of flowchart 450 as presented in FIG. 4B. In an exemplary embodiment, in step 452, labeled ECG data with corresponding beat-level conditions is retrieved from one or more databases. In an exemplary embodiment, conditions may focus on abnormalities in individual beats, not rhythm patterns, and may serve as the ground truth for training the beat condition classification model. In an exemplary embodiment, the labels may include:

Normal Beats: Standard ECG features without abnormalities in the P wave, QRS complex, or T wave.

Premature Atrial Contractions (PACs): Early atrial beats characterized by an abnormal P wave, followed by a normal QRS complex.

Premature Ventricular Contractions (PVCs): Early ventricular beats with a wide and abnormal QRS complex, often lacking a preceding P wave.

In an exemplary embodiment, similar labels may be provided for all additional conditions provided above.

In an exemplary embodiment, step 454 may comprise extracting utilizing beats classifier detailed features extract detailed beat features, such as the onset, peak, and offset of the P wave, QRS complex, and T wave, for each respective heartbeat from each respective ECG of an exemplary training dataset. In an exemplary embodiment, these exemplary labeled beat features may then then be used as inputs to the beat condition classification model to detect specific conditions like normal beats, PACs, and PVCs. That is, trained beats classifier 206 may be utilized to generate values dealing with beat properties for each heartbeat within an ECG.

In an exemplary embodiment, this step may entail utilizing generator 208 to produce quantized vectors representing input ECGs that have been labeled. Accordingly, based on training of RVQ 214 along with beat classifier 206, in an exemplary embodiment, inherently quantified vectors make take into account beat features. Accordingly, in an exemplary scenario, input data may have explicitly beat classifications done utilizing beat classifier 206 or may have these values passed to beats condition classification model 207 which may utilize input labels along with quantized vectors from RVQ 214 or outputs from beast classifier 206 to train.

In an exemplary embodiment, step 456 may comprise training the beat condition classification model 207 by using the beat-level features labeled by the beats classifier 206 and input beast condition labels.

In an exemplary embodiment, exemplary labeled features from the beats classifying model, such as abnormal P waves, wide QRS complexes, or missing T waves, may be mapped to the corresponding beat-based conditions, that is, training process may involve an exemplary model learning to associate specific beat patterns with the predefined conditions (normal, PAC, PVC, etc.), allowing an exemplary model to accurately classify these conditions based on individual waveform characteristics.

In an exemplary embodiment, beats condition classification model 207 may adjust its internal parameters based on the differences between predicted condition labels and the true condition labels in the dataset, that is, it may work towards minimizing a loss function that measures the difference between the predicted beat condition and the labeled beat condition in the second labeled dataset. In an exemplary embodiment, beat condition classification model 207 parameters may be updated using backpropagation during training to optimize classification accuracy for each beat condition. In an exemplary embodiment, a broad range of ECGs may be used to train the model on both normal and abnormal beats, ensuring robustness in detecting different conditions.

Once trained, during inference, in an exemplary embodiment, beat condition classification model 207 may be utilized new ECG data to determine presence of beat based conditions. In an exemplary embodiment, beat condition classification model 207 may take the beat-level features from beats classifier 206 and may output potential conditions such as normal, PAC, or PVC, based on those features alone. By focusing strictly on individual beats, beats condition classifier may accurately identify beat-related anomalies, providing critical insights for diagnosing heart conditions.

In an exemplary embodiment, these classifications may allow clinicians to focus on specific beat-level irregularities in the ECG and applying a clinical solution based on an exemplary beat-based condition. In an exemplary embodiment, applying a clinical solution based on an exemplary beat-based conditions may include alerting a healthcare provider to abnormal heart rhythms or initiating a treatment recommendation. In an exemplary embodiment, clinical solutions may include medications (such as beta blockers) or conduction medical procedures such as ablation.

In another exemplary embodiment, structure 208 may further comprise rhythm classifier 208. In an exemplary embodiment, training and inference for rhythm classifier 208 requires utilizing a trained GAN 204, specifically generator 210 within GAN 204, and even more specifically RVQ 214. In an exemplary embodiment, rhythm classifier 208 may entail classifying ECG rhythms based on temporal patterns in heartbeats, including rhythms such as normal sinus rhythm (NSR), Atrial Fibrillation (AFib), and Atrial Flutter (AFlutter). In an exemplary embodiment, rhythm classifier may incorporate self-attention mechanisms to capture intricate temporal relationships within the ECG signals. In an exemplary embodiment, rhythm classifier may utilize previously trained generator 210 to enhance feature representation and learning.

Figure 5:
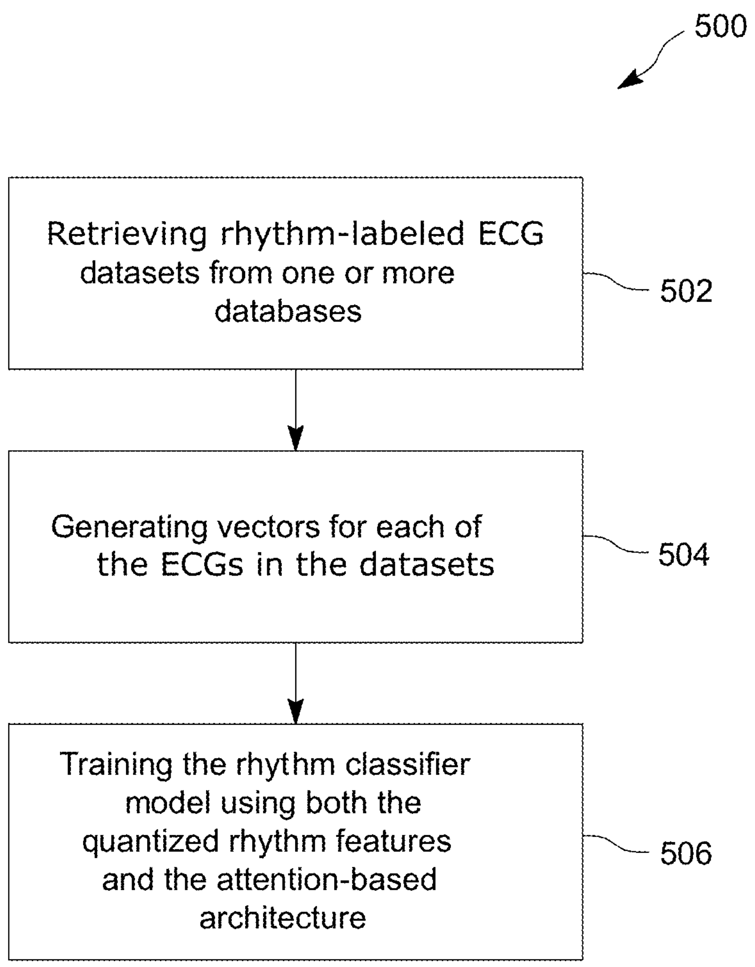
FIG. 5 illustrates a flowchart for method for training a rhythm classifying model, consistent with one or more exemplary embodiments of the present disclosure.

FIG. 5 illustrates a flowchart for method 500 for training a rhythm classifying model, consistent with one or more exemplary embodiments of the present disclosure. In an exemplary embodiment, method 500 may comprise a method for training a rhythm classifying model, consistent with one or more exemplary embodiments of the present disclosure. In an exemplary embodiment, step 502 may comprise retrieving rhythm-labeled ECG datasets from one or more databases. In an exemplary embodiment, these exemplary datasets may provide ground truth labels for various cardiac rhythms:

- Normal Sinus Rhythm (NSR): The standard, healthy rhythm of the heart.
- Atrial Fibrillation (AFib): A rapid, irregular heart rhythm caused by disorganized electrical signals in the atria.
- Atrial Flutter (AFlutter): A fast but regular heart rhythm caused by abnormal circuits in the atria.

In an exemplary embodiment, the exemplary labeled datasets in context of rhythms in ECGs may form the basis for training classifier 208. In an exemplary embodiment, as with any of labels included within exemplary embodiments, labels may be provided by experts, technicians, or physicians.

In an exemplary embodiment, step 504 may entail generating vectors for each of the ECGs in the datasets. In an exemplary embodiment, the residual vector quantizer 214 from the previously trained GAN 204 may be utilized. In an exemplary embodiment, RVQ 214 may help in extracting and compressing critical temporal features from the ECG signals, providing a high-level, discrete representation of the data. In an exemplary embodiment, rhythm classifier 208 may benefit from these quantized features, which may efficiently represent both low-level beat details and high-level temporal dynamics, making it possible to focus on rhythm-specific characteristics.

In an exemplary embodiment, rhythm classifier 208 may apply positional encoding on received set of heartbeats since ECG signal are sequential to maintain order of the beats. In an exemplary embodiment, this may allow for ensuring that that the self-attention mechanism is aware of the timing between beats, which is crucial for identifying rhythm patterns like the regular timing in NSR or the irregular spacing between beats in AFib.

In an exemplary embodiment, positional encoding may be applied using sine and cosine functions of varying wavelengths to embed positional information into each beat, as defined by:

for the sine function, $$PE(pos, 2i) = \sin\left(\frac{(pos)}{}10000^{\frac{2i}{d}}\right) \quad \text{(Equation No. 3)}$$

for the cosine function, $$PE(pos, 2i+1) = \cos\left(\frac{(pos)}{}10000^{\frac{2i}{d}}\right) \quad \text{(Equation No. 4)}$$

wherein pos is position of each beat in a sequence, i is dimension index, and d is total dimensionality of the positional encoding.

In an exemplary embodiment, rhythm classifier may comprise an exemplary transformer that may be an exemplary model that may rely on attention mechanisms to process sequential data. In an exemplary embodiment, unlike traditional recurrent neural networks (RNNs), which process sequences step by step, exemplary transformer may process entire sequences simultaneously, making it highly efficient for ECG signal analysis which may involve long range dependencies. In an exemplary embodiment, during training, a number of labeled heartbeats in an ECG may be provided to rhythm classifier 208, such as 50 beats at a time.

In an exemplary embodiment, the core of the rhythm classifier model may be an attention-based architecture. In an exemplary embodiment, this model may use a self-attention mechanism to focus on specific parts of the ECG signal, learning the relationships between different beats and identifying the rhythm patterns that distinguish NSR, AFib, and AFlutter.

In an exemplary embodiment, an exemplary transformer architecture may compute three vectors for each heartbeat: Query, Key, and Value. The self-attention mechanism may calculate the similarity between the Query and Key vectors to assign attention scores, determining which other beats in the sequence should be most relevant for the current beat.

In an exemplary embodiment, exemplary self-attention mechanism may calculate attention of scores between each individual heartbeat by computing a dot product of Query and Key vectors and scaling the result by the inverse square root of the Key vector dimension, as follows:

$$\text{Attention }(Q, K, V) = softmax\left(\frac{Q\,K^T}{sqrt(d_k)}\right)V \quad \text{(Equation No. 5)}$$

wherein, Q is query vector, K is key vector, V is value vector, and $d_k$ is dimensionality of the key vectors.

In an exemplary embodiment, based on these similarity scores, an exemplary model may calculate attention weights. In an exemplary embodiment, these weights may allow the model to focus on important relationships between distant beats in the ECG sequence. For rhythm classification, this is particularly important in detecting the irregularity of AFib or the fast, repeating patterns in AFlutter.

In an exemplary embodiment, in context of Normal Sinus Rhythm, in an exemplary embodiment, self-attention mechanism may learn to recognize normal Rhythm when consistent PQRST waveforms are identified with regular timing between heartbeats. In an exemplary embodiment, an exemplary transformer may easily identify the regular timing of these features across the ECG sequence, associating them with NSR. In an exemplary embodiment, quantized vectors from QRV 214, based on training phase of GAN 204 and beat classifier 206 may inherently internalize values of PQRST, etc. Accordingly, when labeled ECGs are provided to rhythm classifier 208, indicating various health conditions, exemplary transformer within classifier 208 inherently trains on these values.

In an exemplary embodiment, in context of Atrial Fibrillation (AFib), in an exemplary embodiment, AFib may be characterized by highly irregular timing between heartbeats, lacking distinct P waves, and chaotic electrical signals. In an exemplary embodiment, an exemplary self-attention mechanism may capture these irregularities by focusing on the varying intervals between QRS complexes and the chaotic nature of the atrial signals. In an exemplary embodiment, this allows rhythm classifier 208 to identify the lack of consistency typical of AFib, making it highly effective at detecting this rhythm.

In an exemplary embodiment, in context of Atrial Flutter (AFlutter), AFlutter, unlike AFib, presents a fast but regular rhythm, often appearing as a “sawtooth” pattern due to the rapid atrial contractions. In an exemplary embodiment, exemplary attention mechanism focuses on the regular, rapid appearance of atrial waves, distinguishing it from both AFib and NSR by learning the repetitive nature of the flutter waves.

In an exemplary embodiment, experts or technicians provide labels indicating whether each part of ECG under consideration indicated Normal Rhythm, AFib, or Aflutter.

In an exemplary embodiment, as discussed above, an exemplary self-attention mechanism may be the heart of transformer’s architecture. In an exemplary embodiment, an exemplary self-attention mechanism may allow an exemplary model to weigh the importance of each part of the input sequence (such as ECG beats) when making predictions. This enables the model to learn relationships between different elements of the sequence, regardless of their positions, and focus on the most relevant parts. In an exemplary scenario, in an ECG sequence, an exemplary model might focus on irregularly spaced beats to classify Atrial Fibrillation (AFib) or focus on consistently repeated beats to detect Atrial Flutter (AFlutter).

In an exemplary embodiment, transformers may use residual connections (or “skip connections”) to help the model learn deeper representations. In an exemplary embodiment, these connections may allow the input to bypass certain layers and get added back to the output of those layers, preventing the model from “forgetting” important information. In an exemplary embodiment, self-attention mechanism of an exemplary transformer enables the model to learn relationships between different time steps in the ECG signal. For rhythm classification, this means capturing how beats relate to each other across the entire sequence.

In an exemplary embodiment, step 506 may comprise training the rhythm classifier model is trained using both the quantized rhythm features and the attention-based architecture. During training, the model learns to associate specific temporal patterns with rhythm labels such as NSR, AFib, and AFlutter.

In an exemplary embodiment, an exemplary model comprising utilizing a transformer architecture adjusts its internal parameters by minimizing the difference between its predicted rhythm classifications and the true rhythm labels. The attention mechanism allows the model to handle long sequences and focus on rhythm-specific markers, ensuring robust classification.

In an exemplary embodiment, in detail, during the training process, for all of the positionally encoded data, the positional encoded ECG data may be processed through a multi-head self-attention mechanism to compute attention scores between each beat and other beats in the sequence, wherein the attention mechanism utilizes Query, Key, and Value vectors to capture temporal dependencies between the individual heartbeats. Thereafter, during training, there may be concatenating outputs from multiple attention heads and applying of a linear transformation to generate a transformed representation of the ECG sequence and passing the transformed representation through a feed-forward network comprising one or more layers to refine rhythm-based features. Thereafter, model parameters may be optimized based on a comparison between the predicted rhythm classifications and ground truth rhythm labels in the dataset.

Once trained, during inference, in an exemplary embodiment, an exemplary trained rhythm classifier model, such as rhythm classifier 206, may be applied to new ECG data. In an exemplary embodiment, when a rhythm classifier 208 is to be utilized, an input ECG may first be segmented by utilizing beat segmented 102 and then have quantized vectors generated for each segmented beat utilizing RVQ 114. Utilizing the vector values, an exemplary rhythm classifier model, such as rhythm classifier 208, may evaluate the input ECG represented by the vectors from the residual vector quantizer 214 to infer the likely rhythm as one of NSR, AFib, and Aflutter. In an exemplary embodiment, each respective heartbeat may be labeled as such. In an exemplary embodiment, therefore data may be presented across for each respective heartbeat in an ECG regarding its rhythm status.

In an exemplary embodiment, based on detection of cardiac rhythm condition, medical intervention may be applied. For example, when AFib is determined, medical interventions may focus on controlling the heart rate or rhythm and reducing the risk of stroke. In an exemplary embodiment, treatments may include medications such as beta-blockers, antiarrhythmics, and anticoagulants. In an exemplary embodiment, in more severe cases, procedures like cardioversion, catheter ablation, or the maze procedure may be performed to restore normal heart rhythm or prevent further complications.

Furthermore, for example when AFlutter is detected, medical interventions may aim to control the rapid heart rate and prevent complications like stroke. In an exemplary embodiment, an exemplary treatment may include medications such as beta-blockers, calcium channel blockers, and anticoagulants to manage heart rate and reduce clotting risk. In some cases, cardioversion or catheter ablation may be used to restore normal rhythm by targeting the abnormal circuits causing Aflutter.

Figure 6:
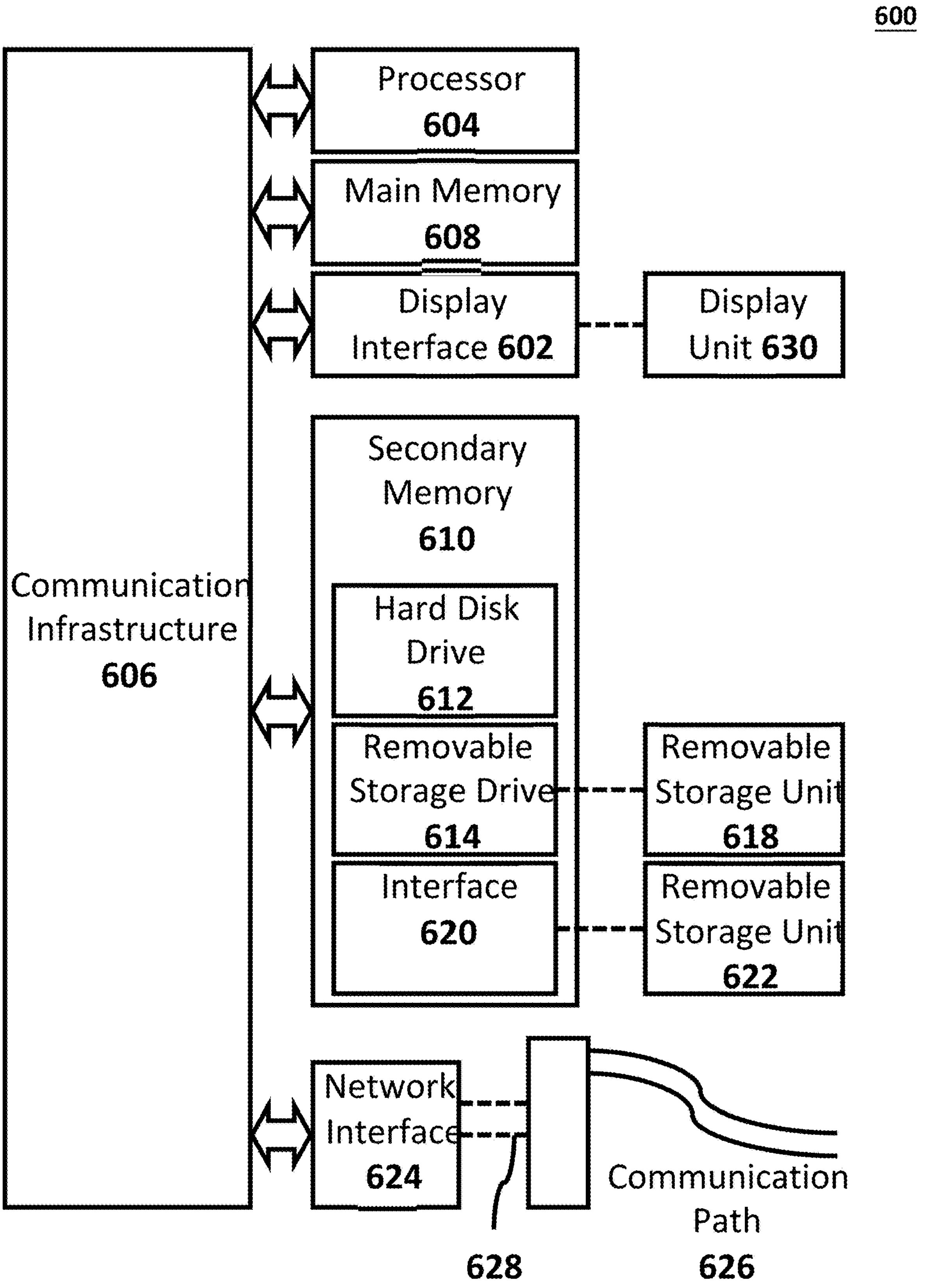
FIG. 6 illustrates an example computer system in which an embodiment of the present invention, or portions thereof, may be implemented as computer-readable code, consistent with exemplary embodiments of the present disclosure.

FIG. 6 illustrates an example computer system 600 in which an embodiment of the present invention, or portions thereof, may be implemented as computer-readable code, consistent with exemplary embodiments of the present disclosure. For example, device 100 may be implemented in computer system 600 using hardware, software, firmware, tangible computer readable media having instructions stored thereon, or a combination thereof and may be implemented in one or more computer systems or other processing systems. Hardware, software, or any combination of such may embody any of the modules and components utilized with respect to the methods described in FIGS. 3-5.

If programmable logic is used, such logic may be executed on a commercially available processing platform or a special purpose device. One of ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 600. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 604 may be a special purpose or a general-purpose processor device. As will be appreciated by persons skilled in the relevant art, processor device 604 may also be a single processor in a multi-core/multiprocessor system, such system operating alone, or in a cluster of computing devices operating in a cluster or server farm. Processor device 604 is connected to a communication infrastructure 606, for example, a bus, message queue, network, or multi-core message-passing scheme.

Computer system 600 also includes a main memory 608, for example, random access memory (RAM), and may also include a secondary memory 610. Secondary memory 610 may include, for example, a hard disk drive 612, removable storage drive 614. Removable storage drive 614 may comprise a floppy disk drive, a magnetic tape drive, an optical disk drive, a flash memory, or the like. The removable storage drive 614 reads from and/or writes to a removable storage unit 618 in a well-known manner. Removable storage unit 618 may comprise a floppy disk, magnetic tape, optical disk, etc., which is read by and written to by removable storage drive 614. As will be appreciated by persons skilled in the relevant art, removable storage unit 618 includes a computer usable storage medium having stored therein computer software and/or data.

In alternative implementations, secondary memory 610 may include other similar means for allowing computer programs or other instructions to be loaded into computer system 600. Such means may include, for example, a removable storage unit 622 and an interface 620. Examples of such means may include a program cartridge and cartridge interface (such as that found in video game devices), a removable memory chip (such as an EPROM, or PROM) and associated socket, and other removable storage units 622 and interfaces 620 which allow software and data to be transferred from the removable storage unit 622 to computer system 600.

Computer system 600 may also include a communications interface 624. Communications interface 624 allows software and data to be transferred between computer system 600 and external devices. Communications interface 624 may include a modem, a network interface (such as an Ethernet card), a communications port, a PCMCIA slot and card, or the like. Software and data transferred via communications interface 624 may be in the form of signals, which may be electronic, electromagnetic, optical, or other signals capable of being received by communications interface 624. These signals may be provided to communications interface 624 via a communications path 626. Communications path 626 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 618, removable storage unit 622, and a hard disk installed in hard disk drive 612. Computer program medium and computer usable medium may also refer to memories, such as main memory 608 and secondary memory 610, which may be memory semiconductors (e.g. DRAMs, etc.).

Computer programs (also called computer control logic) are stored in main memory 508 and/or secondary memory 610. Computer programs may also be received via communications interface 624. Such computer programs, when executed, enable computer system 500 to implement the present invention as discussed herein. In particular, the computer programs, when executed, enable processor device 604 to implement the processes of the present invention, such as the operations in the method illustrated by flowchart 300 of FIG. 3, flowchart 400 of FIG. 4A, flowchart 250 or FIG. 4B, and flowchart 500 of FIG. 5 discussed above. Accordingly, such computer programs represent controllers of the computer system 600. Where the invention is implemented using software, the software may be stored in a computer program product and loaded into computer system 500 using removable storage drive 614, interface 620, and hard disk drive 612, or communications interface 624.

Embodiments of the invention also may be directed to computer program products comprising software stored on any computer useable medium. Such software, when executed in one or more data processing device, causes a data processing device(s) to operate as described herein. An embodiment of the invention employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

Accordingly, in an exemplary embodiment, neural network architecture tailored for ECG signal analysis may be trained to differentiate between noise and true cardiac events. In an exemplary embodiment, exemplary systems may be integrated with ECG Patches and Holter Monitors, allowing for continuous and accurate monitoring of cardiac activity in real-world environments In an exemplary embodiment, alternatively or in addition, the present disclosure (or portions of the system and methods of the present disclosure) may be performed on a local processing device (e.g., a laptop), absent an external server or network.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantially" when used with an adjective or adverb is intended to enhance the scope of the particular characteristic; e.g., substantially planar is intended to mean planar, nearly planar and/or exhibiting characteristics associated with a planar element. Further use of relative terms such as "vertical", "horizontal", "up", "down", and "side-to-side" are used in a relative sense to the normal orientation of the apparatus.

What is claimed:

1. A method for classifying cardiac rhythms in electrocardiogram (ECG) data, the method comprising:

measuring a candidate ECG signal from a patient using a Holter monitor, wherein the Holter monitor is communicatively connected to one or more processors; and using the one or more processors to perform:

receiving a dataset comprising ECG signals and corresponding labels, each of the ECG signals representing a respective sequence of beats, and the corresponding labels indicating cardiac rhythm types for the beats, the cardiac rhythm types including normal sinus rhythm, atrial fibrillation, and atrial flutter;

generating quantized vectors representing the ECG signals by applying a trained neural network encoder and a residual vector quantizer (RVQ) to the ECG signals, the residual vector quantizer trained to compress and encode data into a lower-dimensional space;

positionally encoding the quantized vectors to obtain positionally-encoded quantized vectors;

training a rhythm classifier to classify rhythms of ECG signal beats using the positionally-encoded quantized vectors, the training comprising:

processing the positionally-encoded quantized vectors using a multi-head self-attention mechanism to generate transformed representations of the positionally-encoded quantized vectors, the processing comprising:

computing, for each particular ECG signal of the ECG signals, attention scores between each beat and other beats of the respective sequence of beats represented by the particular ECG signal, wherein the multi-head self-attention mechanism utilizes Query, Key, and Value vectors to capture temporal dependencies among individual beats;

passing the transformed representations through a feed-forward neural network to obtain, for each particular ECG signal of the ECG signals, respective cardiac rhythm classifications for the respective sequence of beats represented by the particular ECG signal, each of the cardiac rhythm classifications indicating a respective one of the cardiac rhythm types; and updating parameters of the rhythm classifier based on a comparison between the cardiac rhythm classifications and the labels in the dataset;

classifying cardiac rhythms of beats in the candidate ECG signal, measured for the patient using the Holter monitor, using the trained rhythm classifier, the classifying comprising:

receiving the candidate ECG signal measured for the patient using the Holter monitor, the candidate ECG signal comprising beats representing respective heartbeats of the patient;

generating candidate quantized vectors for the candidate ECG signal by applying the trained neural network encoder and the residual vector quantizer to the candidate ECG signal;

positionally encoding the candidate quantized vectors to obtain positionally-encoded candidate quantized vectors; and classifying the rhythms of the beats in the candidate ECG signal into respective cardiac rhythm types selected from among the cardiac rhythm types, the classifying comprising:

generating transformed representations of the positionally-encoded candidate quantized vectors by processing the positionally-encoded candidate quantized vectors using the multi-head self-attention mechanism; and passing the transformed representations through the feed-forward neural network to obtain cardiac rhythm classifications of the beats in the candidate ECG signal; and generating an output indicating the cardiac rhythm classifications of the beats in the candidate ECG signal measured for the patient using the Holter monitor.

2. The method of claim 1, wherein the multi-head self-attention mechanism computes the attention scores between each beat and the other beats of the respective sequence of beats represented by the particular ECG signal by computing a dot product of the Query and Key vectors and scaling the dot product by an inverse square root of a dimension of the Key vector, as follows:

$$\text{Attention}(Q, K, V) = softmax\left(\frac{Q K^T}{sqrt(d_k)}\right)V,$$

wherein, Q is the Query vector, K is the Key vector, V is the Value vector, and $d_k$ is the dimension of the Key vector.

3. The method of claim 1, wherein positionally encoding the candidate quantized vectors to obtain the positionally-encoded candidate quantized vectors comprises:

using sine and cosine functions of varying wavelengths to embed positional information of beats in the respective sequence of beats represented by the particular ECG signal.

4. The method of claim 1, further comprising one or more residual connection applied between an input of the multi-head self-attention mechanism and an output of the feed-forward neural network.

5. The method of claim 1, wherein updating the parameters of the rhythm classifier based on the comparison between the cardiac rhythm classifications and the labels in the dataset comprises updating the parameters using back-propagation based on a loss function that measures differences between the cardiac rhythm classifications and the labels.

6. The method of claim 1, further comprising, when one or more of the rhythms of the beats in the candidate ECG signal are classified into the atrial fibrillation or the atrial flutter cardiac rhythm, generating an alert indicating an abnormal cardiac rhythm.

7. The method of claim 1, further comprising, when one or more of the rhythms of the beats in the candidate ECG signal are classified into the atrial fibrillation or the atrial flutter cardiac rhythms, initiating a recommendation to administer one or more treatments selected from among: a beta-blocker, an antiarrhythmic, an anticoagulant, a cardioversion, a catheter ablation, a maze procedure, and a calcium channel blocker.

8. The method of claim 1, further comprising identifying wave properties of the beats in the candidate ECG signal by using a trained beat classifier to process the quantized vectors, the wave properties including one or more of P wave: onset, peak, and offset, Q wave: peak, R wave: peak, S wave: peak, T wave: onset, peak, and offset, U wave: peak and offset, and QRS complex: onset and offset.

9. The method of claim 1, further comprising processing the quantized vectors using a trained waveform classifier to obtain waveform labels for the candidate ECG signal.

10. A method for classifying cardiac rhythms in an electrocardiogram (ECG) signal measured for a patient, the method comprising:

measuring the ECG signal for the patient using a Holter monitor, the ECG signal comprising a sequence of beats representing a corresponding sequence of heartbeats of the patient, wherein the Holter monitor is communicatively connected to one or more processors; and using the one or more processors to perform:

receiving the ECG signal measured for the patient using the Holter monitor;

generating a set of quantized vectors by applying a trained neural network encoder and residual vector quantizer (RVQ) to the ECG signal measured for the patient using the Holter monitor, wherein the residual vector quantizer is trained to compress and encode the ECG signal into a lower-dimensional space;

positionally encoding the set of quantized vectors to obtain a set of positionally-encoded quantized vectors;

classifying rhythms of beats in the sequence of beats by processing the set of positionally-encoded quantized vectors using a trained rhythm classifier having a transformer architecture including multiple self-attention heads and a feed-forward neural network to generate classification results indicating, for each of the beats in the sequence of beats, a respective cardiac rhythm from among: normal sinus rhythm, atrial fibrillation, or atrial flutter; and generating an output indicating the classification results indicating the respective cardiac rhythm for each of the beats in the sequence of beats of the ECG signal measured for the patient using the Holter monitor.

11. The method of claim 10, wherein positionally encoding the set of quantized vectors to obtain the set of positionally-encoded quantized vectors comprises:

using sine and cosine functions of varying wavelengths to embed positional information of the beats in the sequence of beats.

12. The method of claim 10, wherein the multiple self-attention heads compute attention scores between each beat and other beats in the sequence of beats by computing a dot product of Query and Key vectors and scaling the dot product by an inverse square root of a dimension of the Key vector, as follows:

$$\text{Attention}(Q, K, V) = \mathit{soft}\max\left(\frac{Q\,K^T}{sqrt(d_k)}\right)V,$$

wherein, Q is the Query vector, K is the Key vector, V is a Value vector, and $d_k$ is the dimension of the Key vector.

13. The method of claim 10, wherein the rhythm classifier is trained using backpropagation to update parameters of the rhythm classifier based on a loss function that measures differences between cardiac rhythm classifications for beats of ECG signals and corresponding labels, the corresponding labels indicating cardiac rhythm types for the beats of the ECG signals.

14. The method of claim 10, wherein the trained rhythm classifier utilizes residual connections applied between an input of the transformer architecture and an output of the transformer architecture.

15. The method of claim 10, further comprising, when one or more of the rhythms of the beats in the sequence of beats are classified into the atrial fibrillation or the atrial flutter cardiac rhythm, generating an alert indicating an abnormal cardiac rhythm.

16. The method of claim 10, further comprising, when one or more of the rhythms of the beats in the sequence of beats are classified into the atrial fibrillation or the atrial flutter cardiac rhythm, initiating a recommendation to administer one or more treatments selected from among: a beta-blocker, an antiarrhythmic, an anticoagulant, a cardioversion, a catheter ablation, a maze procedure, and a calcium channel blocker.

17. The method of claim 10, further comprising processing the set of quantized vectors using a trained decoder neural network to obtain a clean ECG signal.

18. The method of claim 10, further comprising identifying wave properties of the beats in the sequence of beats by using a trained beat classifier to process the set of quantized vectors, the wave properties including one or more of P wave: onset, peak, and offset, Q wave: peak, R wave: peak, S wave: peak, T wave: onset, peak, and offset, U wave: peak and offset, and QRS complex: onset and offset.

19. A system, comprising:

a Holter monitor configured to measure an electrocardiogram (ECG) signal for a patient, the ECG signal comprising a sequence of beats representing a corresponding sequence of heartbeats of the patient;

one or more processors communicatively coupled to the Holter monitor; and at least one non-transitory computer-readable storage medium storing processor-executable instructions that, when executed by the one or more processors, cause the one or more processors to perform a method for classifying cardiac rhythms in the ECG signal measured for the patient, the method comprising:

receiving the ECG signal, measured for the patient using the Holter monitor, the ECG signal comprising a sequence of beats representing a corresponding sequence of heartbeats of the patient;

generating a set of quantized vectors by applying a trained neural network encoder and residual vector quantizer (RVQ) to the ECG signal measured for the patient using the Holter monitor, wherein the residual vector quantizer is trained to compress and encode the ECG signal into a lower-dimensional space;

positionally encoding the set of quantized vectors to obtain a set of positionally-encoded quantized vectors;

classifying rhythms of beats in the sequence of beats by processing the set of positionally-encoded quantized vectors using a trained rhythm classifier having a transformer architecture including multiple self-attention heads and a feed-forward neural network to generate classification results indicating, for each of the beats in the sequence of beats, a respective cardiac rhythm from among: normal sinus rhythm, atrial fibrillation, or atrial flutter; and generating an output indicating the classification results indicating the respective cardiac rhythm for each of the beats in the sequence of beats of the ECG signal measured for the patient using the Holter monitor.

* * * * *